US008840978B2

(12) United States Patent
Taghavi

(10) Patent No.: US 8,840,978 B2
(45) Date of Patent: Sep. 23, 2014

(54) IDENTIFICATION DEVICE HAVING ANTIMICROBIAL PROPERTIES

(71) Applicant: Precision Dynamics Corporation, Valencia, CA (US)

(72) Inventor: Shane Taghavi, Woodland Hills, CA (US)

(73) Assignee: Precision Dynamics Corporation, Valencia, CA (US)

( * ) Notice: Subject to any disclaimer, the term of this patent is extended or adjusted under 35 U.S.C. 154(b) by 0 days.

(21) Appl. No.: 13/658,197

(22) Filed: Oct. 23, 2012

(65) Prior Publication Data

US 2013/0101758 A1  Apr. 25, 2013

Related U.S. Application Data

(60) Provisional application No. 61/550,685, filed on Oct. 24, 2011.

(51) Int. Cl.

| | |
|---|---|
| *B32B 9/00* | (2006.01) |
| *B32B 33/00* | (2006.01) |
| *B41M 5/42* | (2006.01) |
| *A61K 8/02* | (2006.01) |
| *G09F 7/02* | (2006.01) |
| *B41M 5/337* | (2006.01) |
| *B41M 5/41* | (2006.01) |
| *G09F 3/00* | (2006.01) |
| *G09F 3/10* | (2006.01) |
| *B41M 5/32* | (2006.01) |

(52) U.S. Cl.
CPC .............. *B41M 5/426* (2013.01); *A61K 8/0208* (2013.01); *G09F 7/02* (2013.01); *B41M 5/32* (2013.01); *B41M 5/3377* (2013.01); *B41M 5/41* (2013.01); *G09F 3/00* (2013.01); *G09F 3/005* (2013.01); *G09F 3/10* (2013.01); *B41M 2205/04* (2013.01); *B41M 2205/40* (2013.01)
USPC ........................................ 428/40.1; 424/443

(58) Field of Classification Search
CPC ............ G09F 3/10; G09F 7/02; A61K 8/0208
USPC ........................................ 428/40.1; 424/443
See application file for complete search history.

(56) References Cited

U.S. PATENT DOCUMENTS

| | | | |
|---|---|---|---|
| 4,260,677 A | 4/1981 | Winslow et al. | |
| 4,504,575 A | 3/1985 | Lee | |
| 4,906,466 A | 3/1990 | Edwards et al. | |
| 5,536,696 A | 7/1996 | Horsten et al. | |
| 6,013,275 A | 1/2000 | Konagaya et al. | |
| 7,910,204 B2 | 3/2011 | Hartman et al. | |
| 2003/0215521 A1 | 11/2003 | Laridon et al. | |
| 2006/0248767 A1 | 11/2006 | Hofer et al. | |
| 2007/0141125 A1 | 6/2007 | Bourdelais et al. | |
| 2009/0035342 A1 | 2/2009 | Karandikar et al. | |
| 2009/0068412 A1 | 3/2009 | Nahmias et al. | |
| 2009/0130157 A1 | 5/2009 | Ylitalo et al. | |
| 2009/0286033 A1 | 11/2009 | Taghavi et al. | |
| 2009/0291147 A1 | 11/2009 | Sandford et al. | |
| 2009/0301382 A1 | 12/2009 | Patel | |
| 2010/0034900 A1 | 2/2010 | Temchenko et al. | |
| 2010/0104791 A1 | 4/2010 | Baudrion et al. | |

FOREIGN PATENT DOCUMENTS

JP  9274435 A  10/1997

*Primary Examiner* — Betelhem Shewareged
(74) *Attorney, Agent, or Firm* — Kelly & Kelley, LLP

(57) ABSTRACT

An identification device, preferably a wristband or adhesive label, is configured to receive identifying indicia by means of a direct thermal printer. A direct thermal layer includes antimicrobial particles embedded therein and is exposed, i.e., does not have a protective overcoat or varnish covering the direct thermal layer. The antimicrobial particles increase the surface available silver ions and are preferably formed of an aqueous dispersion of silver chloride-coated titanium dioxide particles. The antimicrobial particles may also be formed of an inorganic silver-containing compound such as silver zirconium phosphates or a silver substituted zeolite.

28 Claims, 1 Drawing Sheet

IDENTIFICATION DEVICE HAVING ANTIMICROBIAL PROPERTIES

BACKGROUND OF THE INVENTION

The present invention is directed to an identification device, preferably a wristband or an adhesive label, comprising a direct thermal printable surface having antimicrobial properties. Specifically, the identification device is configured for receiving identification information by means of a direct thermal printer and having antimicrobial properties without the use of a protective layer or overcoat on top of the direct thermal layer.

Direct thermal printable media is used in printers and in other applications requiring permanent imaging such as wristbands, tags, labels and other identification media. In contrast to printing technologies that involve the transfer of ink from one location to another, direct thermal printing uses a special printable media that incorporates a color developing mechanism. Images are formed by exposing the color developing mechanism to concentrations of heat that produce localized chemical reactions involving a change of color (usually light to dark). The color developing mechanism is provided by a thermosensitive imaging material containing heat reactive chemicals such as leuco dyes or metallic salts.

Since direct thermal printing only involves the transfer of heat, printing of direct thermal media is simple and clean. Other advantages include low cost, low noise, and high speed. The thermosensitive imaging material is typically applied as a layer on top of a substrate surface. Printing takes place by exposing the coating to a pattern of heat conducted from a thermal print head located adjacent to the substrate surface containing the coating of thermosensitive imaging material.

There has been a great deal of attention in recent years given to the hazards of bacterial contamination from potential everyday exposure. Noteworthy examples of such concern include the fatal consequences of food poisoning due to certain strains of *Eschericia coli* being found within undercooked beef in fast food restaurants; *Salmonella* contamination causing sicknesses from undercooked and unwashed poultry food products; and illnesses and skin infections attributed to *Staphylococcus aureus*, yeast, and other unicellular organisms. With such an increased consumer interest in this area, manufacturers have begun introducing antimicrobial agents within various products and articles.

Silver-containing inorganic microbiocides have recently been developed and utilized as antimicrobial agents on and within a plethora of different substrates and surfaces. In particular, such microbiocides have been adapted for incorporation within plastic compositions and fibers in order to provide household and consumer products which inherently exhibit antimicrobial characteristics. Although such silver-based agents provide suitable antimicrobial properties within thermoplastic articles, and other types of articles, there are certain limitations as to the potential antimicrobial efficacy of such thermoplastic articles. Such limitations are apparently due to relatively low amounts of surface-available silver within and/or on such thermoplastic articles. Without intending to be bound to any specific scientific theory, it is believed that such low surface-available amounts of silver are the result of the inability of a sufficient amount of the integrated silver compounds to migrate to the thermoplastic surface. Such a result is observed for standard thermoplastics comprising silver-containing antimicrobials. Thus, there exists a need to provide efficacious amounts of silver-containing antimicrobial agents within thermoplastic compositions that exhibit such heretofore unattainable high levels of surface-available silver compounds, thereby providing more effective antimicrobial activity, among other potential desirable characteristics as a result thereof.

Past plastic compositions and articles comprising silver-containing antimicrobial agents include U.S. Pat. No. 5,405,644 to Ohsumi et al., which includes the addition of certain triazoles; U.S. Pat. No. 4,938,955 to Niira, et al. (also including benzotriazole stabilizers); U.S. Pat. No. 5,750,609 to Nosu et al., which discloses an ultraviolet protective agent for incorporation within a variety of compositions, such as films, fibers, cosmetics, and the like, comprising a zinc-based hydrotalcite which acts solely as an ultraviolet absorber. However, these particular methods and plastics have proven to be costly (with the high expense of benzotriazoles initially), particularly since relatively high concentrations of the expensive stabilizing compounds are required, and do not provide any appreciable increase of available silver on the surface of such articles. Also, as these stabilizers are not thermally stable, they introduce additional processing complications. As such, there is no teaching or fair suggestion within the prior art which pertains to the needed improvement in increasing the amounts of surface-available silver compounds on target thermoplastics.

Another such prior art product includes the Zebra antimicrobial wristband. The Zebra product has the antimicrobial material within a varnish applied on top of the direct thermal material in a secondary process as disclosed in U.S. Patent Publication No. 2006/0248767. There are several disadvantages to using an antimicrobial varnish as in the Zebra product, including: inconsistent printing due to variation in the varnish thickness, discoloration of the varnish when exposed to UV light, shorter print head life, build-up of the varnish on printer rollers, and relatively lower speeds/higher heat energy requirement for the printing process.

Accordingly, there is a need for an identification device configured for receiving identifying indicia by means of a direct thermal printer and that exhibits antimicrobial properties without the associated disadvantages of an overcoat or varnish. The present invention fulfills these needs and provides other related advantages.

SUMMARY OF THE INVENTION

The present invention is directed to an identification device such as a label or a wristband that has a direct thermal reactive layer with inherent antimicrobial properties achieved without the use of a coating or varnish over the direct thermal reactive layer. The inherent antimicrobial properties are achieved by embedding an antimicrobial additive into the direct thermal reactive layer itself. In this way, the direct thermal reactive layer does not require a varnish or overcoat to protect the identification device by inhibiting bacterial growth on the surface of the label or wristband.

In a particular embodiment, the identification device includes a wristband or a label having a direct thermal face stock that has antimicrobial properties without the requirement of an additional coating or varnish layer to protect against microbial growth. The antimicrobial properties are achieved by embedding an antimicrobial additive directly into the direct thermal layer chemistry during manufacture of the direct thermal face stock. The antimicrobial additives may include an aqueous dispersion of silver chloride-coated titanium dioxide particles. The inorganic nature, small particle size, and high temperature tolerance of this "non-nano silver" antimicrobial chemistry makes it ideal for use in a wide range of printing applications. The antimicrobial direct thermal layer of an inventive identification device such as a wristband or label provides for a release of silver ions on demand, which safely inhibit bacterial growth on the identification device. There are numerous advantages to this inventive configuration, such as: no need for a varnish or overcoat to provide antimicrobial protection, a longer print head life, lower energies and higher speeds for printing processes, no buildup on the printer rollers, as well as consistent printability, scanability and readability.

An identification device according to the present invention has an exposed direct thermal layer with inherent antimicrobial properties. In reference to the direct thermal layer, "exposed" means that the direct thermal layer is the top most layer on the identification device, without a varnish or overcoat, such that it is exposed to the environment. Because the direct thermal layer is exposed, it comes into direct contact with environmental elements, i.e., air, water, fluids, dust, dirt, etc.

The identification device, such as a bracelet or a label, has a substrate and an exposed direct thermal layer bonded to the substrate by an adhesive. An antimicrobial material is embedded within the direct thermal layer so as to impart antimicrobial properties thereto. The antimicrobial material preferably comprises an inorganic silver-containing compound, which may include silver chloride-coated titanium dioxide, silver zirconium phosphate, a silver substituted zeolite, or silver-containing glass particles. In the case of the silver chloride-coated titanium dioxide, it is preferably prepared in an aqueous dispersion. The antimicrobial material preferably comprises 0.01% to 10% by weight of the identification device, and more preferably 0.5% to 2% by weight of the identification device.

The direct thermal layer preferably includes, from bottom to top: a base layer, an under layer, a thermal reactive layer; and a barrier layer, wherein the antimicrobial material is dispersed throughout the barrier layer. The base layer may be paper, face stock, label stock, or polymer material, such as polypropylene, polyethylene, or polyester. The substrate of the identification device may be made from glassine, polycoated kraft, calendared kraft, a thermoplastic elastomer, polypropylene, polyethylene, polyethylene terephthalate, polystyrene or a multilayer combination thereof. A release coating may be included between the substrate and the adhesive so as to make the substrate separable from the direct thermal layer.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE INVENTION

The present invention is directed to an identification device, preferably a bracelet or an adhesive label, having an exposed direct thermal layer configured for receiving identifying indicia by means of a direct thermal printer. The direct thermal layer also contains an antimicrobial additive that inhibits the growth of bacteria on the surface of the identification device. Such antimicrobial additives preferably increase the surface available silver on the identification device. In this invention, "bracelet" means a looped device configured to encircle a wrist, ankle or other appendage of a person. Examples include wristbands, anklets and similar devices.

Nowhere within the prior art has such a specific plastic article or method of making thereof been disclosed, utilized, or fairly suggested to produce a thermoplastic article with such desirable increased surface-available silver characteristics.

Any plastic in which a silver-based antimicrobial agent may be properly incorporated can be utilized in this invention. For instance, and without intending any limitations therein, polyolefins, such as polyethylene, polypropylene, and polybutylene, styrenics, such as polystyrene, ABS, and the like, and polyesters, such as polyethylene terephthalate, may be utilized within this invention. Preferably, the plastic is a thermoplastic that can be molded into different shapes and sizes upon extrusion with the silver-containing antimicrobial. Thus, polyolefins, particularly polypropylene, and styrenics, particularly polystyrene, are preferred. Furthermore, such plastics preferably may be colored to provide other aesthetic features for the end user. Thus, the plastic may also comprise colorants, such as, for example, poly(oxyalkylenated) colorants, pigments, dyes, and the like, too. Other additives may also be present, including antistatic agents, brightening compounds, nucleating agents, clarifying agents, lubricants, flame retardants, antioxidants, UV stabilizers, fillers, and the like.

Figure 1:
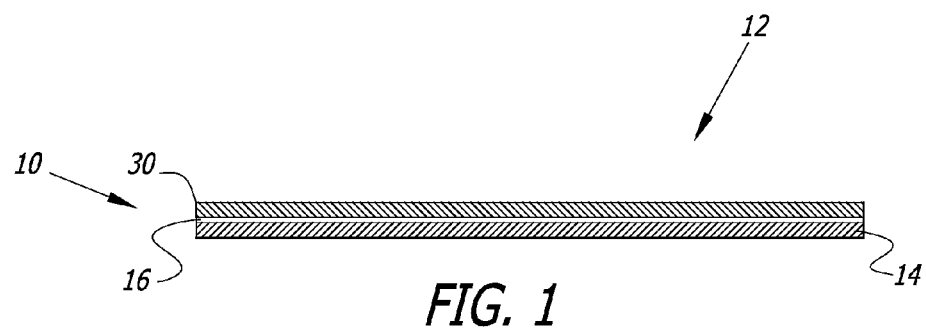
FIG. 1 illustrates the laminated construction of the wristband of the present invention.
Figure 2:
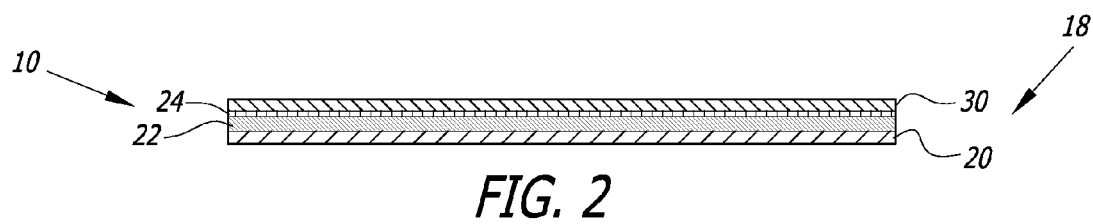
FIG. 2 illustrates the laminated construction of an adhesive label of the present invention.

The identification device 10 of the present invention is a laminated structure as generally depicted in FIGS. 1 and 2 and may come in the form of a wristband 12 or an adhesive label 18. The identification device 10 may be embodied in other structures besides the wristband and label as described herein. The laminated layers of the various figures are illustrated in exaggerated thicknesses for clarity and ease of explanation. In actual construction, the layers have thicknesses typical in laminated constructions of the type described herein.

In FIG. 1, the wristband 12 is illustrated with a substrate layer 14 with an adhesive layer 16 disposed thereon and an exposed direct thermal layer 30 on top of that. To say that the direct thermal layer 30 is exposed means that it is not covered by a varnish or overcoat and capable of coming into contact with environmental contaminants. In this construction, the adhesive layer 16 secures the direct thermal layer 30 to the substrate layer 14 forming the described laminate. The substrate 14, may take the form of a synthetic monolayer comprising thermoplastic elastomers (TPEs), polypropylene (PP), polyethylene (PE), polyethylene terephthalate (PET), or polystyrene (PS). Alternatively, the substrate 14 may comprise a synthetic multilayer or a prelaminated polymeric structure including a combination of TPE, PP, PE, PET, and/or PS. The adhesive layer 16 may comprise a water-based adhesive, a UV-based adhesive, or a hot melt adhesive. The construction of the direct thermal layer 30 will be described more fully below.

FIG. 2 illustrates a sample construction for a label 18. In this construction, the label 18 includes, in order from bottom to top, a liner layer 20, a release coating 22, an adhesive layer 24 and the direct thermal layer 30. The liner layer 20 may comprise a synthetic material, such as PP, PET, PE or similar materials, glassine, polycoated kraft, or calendared kraft. The release coating 22 may comprise a solventless silicone, an emulsion silicone, or a solvent silicone. As with the wristband 12, the adhesive layer 24 of the label 18 may comprise a water-based adhesive, a UV-based adhesive, or a hot melt adhesive. The direct thermal layer 30 of the label 18 is as described below.

Figure 3:
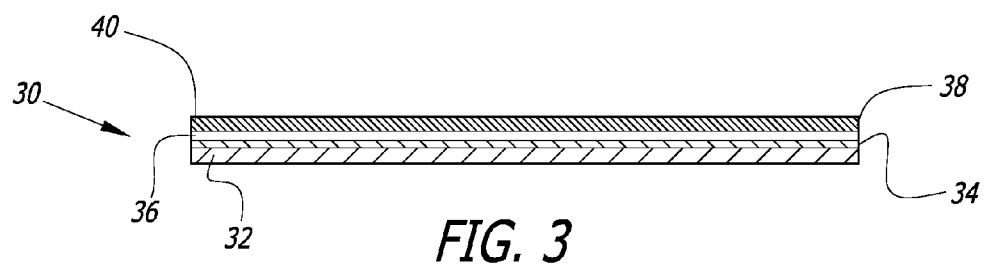
FIG. 3 illustrates the layered construction of the direct thermal layer of the present invention.

FIG. 3 illustrates the construction of the novel direct thermal layer 30 of the present invention. In this construction, the direct thermal layer 30 starts with a base layer 32 that may comprise paper material, synthetic material, face stock, or label stock. The synthetic material may comprise PP, PE, polyester, or similar polymeric compounds. An under layer 34 is deposited on top of the base layer 32. The under layer 34 provides heat insulation and bonding enhancement for the construction of the direct thermal layer 30 and is the primary layer responsible for providing a smooth surface.

A thermal reactive layer 36 is deposited on top of the under layer 34. The thermal reactive layer 36 is the portion of the direct thermal layer 30 that provides the imaging in response to the thermal print head. The thermal reactive layer 36 includes thermal imaging particles and thermal image preservation materials. The thermal imaging layer 36 is a construction known in the art and includes color formers, co-reactants, desensitizers, dispersants, defoamers, lubricants, and such other compounds as are known to those skilled in the art. The thermal image preservation materials include pigments, binders and such other materials as are known to aid in image preservation. Finally, a barrier layer 38 is deposited on top of the thermal reactive layer 36.

The barrier layer 38 preserves the direct thermal layer 30 against moisture, hand sanitizer, alcohol and other such solvents. The barrier layer 38 also acts as a thermal printer head matching layer to achieve even and uniform imaging on the underlying thermal reactive layer 36. The barrier layer 38 has embedded therein antimicrobial particles 40 configured to release silver ions as described herein. The antimicrobial particles 40 are dispersed throughout the barrier layer 38 and preferably comprise an aqueous dispersion of silver chloride-coated titanium dioxide particles.

Another preferred silver-containing antimicrobial is an inorganic silver-containing compound, including, without limitation, inorganic compounds such as silver zirconium phosphates available from Milliken & Company under the tradename ALPHASAN® RC-2000, RC-5000, and RC 7000, although any silver-containing inorganic antimicrobial agent may also be utilized within the inventive plastic article (for instance, as mere examples, a silver substituted zeolite available from Shingawa under the tradename ZEOMIC®, and silver-containing glasses, such as IONPURE® from Ishizuka Glass under the tradename IONPURE®, as well as AMP® T558 and MICROFREE®, both available from DuPont, as well as JMAC®, available from Johnson Mathey). Generally, such an antimicrobial is added in an amount of from about 0.01 to 10% by total weight of the target plastic composition; more preferably from about 0.05 to about 2.0%; and most preferably from about 0.5 to about 2.0%.

Although several embodiments have been described in detail for purposes of illustration, various modifications may be made without departing from the scope and spirit of the invention.

What is claimed is:

1. An identification device having an exposed direct thermal layer with inherent antimicrobial properties, comprising:
    a substrate;
    an exposed direct thermal layer bonded to the substrate by an adhesive and configured to receive identifying indicia by direct thermal printing;
    a release coating between the substrate and the adhesive; and
    an antimicrobial material embedded within the direct thermal layer so as to impart antimicrobial properties thereto.

2. The identification device of claim 1, wherein the antimicrobial material comprises an inorganic silver-containing compound.

3. The identification device of claim 2, wherein the inorganic silver-containing compound comprises silver chloride-coated titanium dioxide, silver zirconium phosphate, a silver substituted zeolite, or silver-containing glass particles.

4. The identification device of claim 3, wherein the silver chloride-coated titanium dioxide is an aqueous dispersion.

5. The identification device of claim 1, wherein the antimicrobial material comprises 0.01% to 10% by weight of the identification device.

6. The identification device of claim 5, wherein the antimicrobial material comprises 0.5% to 2% by weight of the identification device.

7. The identification device of claim 1, wherein the direct thermal layer comprises a base layer of paper, face stock, label stock, or polymer material.

8. An identification device having an exposed direct thermal layer with inherent antimicrobial properties, comprising:
    a substrate;
    an exposed direct thermal layer bonded to the substrate by an adhesive and configured to receive identifying indicia by direct thermal printing; and
    an antimicrobial material embedded within the direct thermal layer so as to impart antimicrobial properties thereto;
    wherein the direct thermal layer comprises a base layer of paper, face stock, label stock, or polymer material; and
    wherein the polymer material comprises polypropylene, polyethylene, or polyester.

9. The identification device of claim 1, wherein the substrate comprises glassine, polycoated kraft, calendared kraft, a thermoplastic elastomer, polypropylene, polyethylene, polyethylene terephthalate, polystyrene or a multilayer combination thereof.

10. The identification device of claim 1, wherein the identification device comprises a bracelet or a label.

11. An identification device having an exposed direct thermal layer with inherent antimicrobial properties, comprising:
    a substrate;
    an exposed direct thermal layer bonded to the substrate by an adhesive and configured to receive identifying indicia by direct thermal printing; and
    an antimicrobial material embedded within the direct thermal layer so as to impart antimicrobial properties thereto;
    wherein the direct thermal layer comprises, from bottom to top: a base layer, an under layer, a thermal reactive layer; and a barrier layer, wherein the antimicrobial material is dispersed throughout the barrier layer.

12. An identification device having an exposed direct thermal layer with inherent antimicrobial properties, comprising:
    a substrate;
    an exposed direct thermal layer bonded to the substrate by an adhesive and configured to receive identifying indicia by direct thermal printing, wherein the direct thermal layer comprises a base layer of paper, face stock, label stock, or polymer material, wherein the polymeric material comprises polypropylene, polyethylene, or polyester; and
    an inorganic silver-containing compound embedded within the direct thermal layer so as to impart antimicrobial properties thereto, wherein the inorganic silver-containing compound comprises 0.01% to 10% by weight of the identification device.

13. The identification device of claim 12, wherein the inorganic silver-containing compound comprises silver chloride-coated titanium dioxide, silver zirconium phosphate, a silver substituted zeolite, or silver-containing glass particles.

14. The identification device of claim 13, wherein the silver chloride-coated titanium dioxide is an aqueous dispersion.

15. The identification device of claim 12, wherein the inorganic silver-containing compound comprises 0.5% to 2% by weight of the identification device.

16. The identification device of claim 12, wherein the substrate comprises glassine, polycoated kraft, calendared kraft, a thermoplastic elastomer, polypropylene, polyethylene, polyethylene terephthalate, polystyrene or a multilayer combination thereof.

17. An identification device having an exposed direct thermal layer with inherent antimicrobial properties, comprising:
a substrate;
an exposed direct thermal layer bonded to the substrate by an adhesive and configured to receive identifying indicia by direct thermal printing;
an inorganic silver-containing compound embedded within the direct thermal layer so as to impart antimicrobial properties thereto, wherein the inorganic silver-containing compound comprises 0.01% to 10% by weight of the identification device; and
a release coating between the substrate and the adhesive.

18. The identification device of claim 12, wherein the identification device comprises a bracelet or a label.

19. An identification device having an exposed direct thermal layer with inherent antimicrobial properties, comprising:
a substrate;
an exposed direct thermal layer bonded to the substrate by an adhesive and configured to receive identifying indicia by direct thermal printing; and
an inorganic silver-containing compound embedded within the direct thermal layer so as to impart antimicrobial properties thereto, wherein the inorganic silver-containing compound comprises 0.0 to 10% by weight of the identification device;
wherein the direct thermal layer comprises, from bottom to top: a base layer, an under layer, a thermal reactive layer; and a barrier layer, wherein the antimicrobial material is dispersed throughout the barrier layer.

20. An identification bracelet or label having an exposed direct thermal layer with inherent antimicrobial properties, comprising:
a substrate;
an exposed direct thermal layer bonded to the substrate by an adhesive, wherein the direct thermal layer comprises, from bottom to top: a base layer, an under layer, a thermal reactive layer; and a barrier layer; and
an antimicrobial material dispersed throughout the barrier layer of the direct thermal layer so as to impart antimicrobial properties thereto.

21. The identification device of claim 20, wherein the antimicrobial material comprises an inorganic silver-containing compound.

22. The identification device of claim 21, wherein the inorganic silver-containing compound comprises silver chloride-coated titanium dioxide, silver zirconium phosphate, a silver substituted zeolite, or silver-containing glass particles.

23. The identification device of claim 22, wherein the silver chloride-coated titanium dioxide is an aqueous dispersion.

24. The identification device of claim 20, wherein the antimicrobial material comprises 0.01% to 10% by weight of the identification device.

25. The identification device of claim 24, wherein the antimicrobial material comprises 0.5% to 2% by weight of the identification device.

26. The identification device of claim 20, wherein the direct thermal layer comprises a base layer of paper, face stock, label stock, polypropylene, polyethylene, or polyester.

27. The identification device of claim 20, wherein the substrate comprises glassine, polycoated kraft, calendared kraft, a thermoplastic elastomer, polypropylene, polyethylene, polyethylene terephthalate, polystyrene or a multilayer combination thereof.

28. The identification device of claim 20, further comprising a release coating between the substrate and the adhesive.

* * * * *

UNITED STATES PATENT AND TRADEMARK OFFICE
CERTIFICATE OF CORRECTION

PATENT NO. : 8,840,978 B2
APPLICATION NO. : 13/658197
DATED : September 23, 2014
INVENTOR(S) : Shane Taghavi It is certified that error appears in the above-identified patent and that said Letters Patent is hereby corrected as shown below:

In the Claims,

In column 7, line 41 (line 10 of claim 19), replace "0.0" with -- 0.01% --.

Signed and Sealed this
Sixth Day of January, 2015

Michelle K. Lee
*Deputy Director of the United States Patent and Trademark Office*